United States Patent
Okandan et al.

(10) Patent No.: US 6,645,757 B1
(45) Date of Patent: Nov. 11, 2003

(54) APPARATUS AND METHOD FOR TRANSFORMING LIVING CELLS

(75) Inventors: Murat Okandan, Albuquerque, NM (US); Paul C. Galambos, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/779,164

(22) Filed: Feb. 8, 2001

(51) Int. Cl.[7] ................................................ C12M 1/00
(52) U.S. Cl. ............................... 435/285.1; 435/285.2; 435/286.1; 435/286.5; 435/288.5; 204/164; 204/403.01; 204/409
(58) Field of Search ........................... 435/285.1, 285.2, 435/286.1, 286.5, 288.5; 204/164, 403.01, 409

(56) References Cited

U.S. PATENT DOCUMENTS

| | | | |
|---|---|---|---|
| 4,945,050 A | 7/1990 | Sanford | 435/172.1 |
| 5,128,257 A | 7/1992 | Baer | 435/173 |
| 5,137,817 A | 8/1992 | Busta | 435/173 |
| 5,262,128 A | * 11/1993 | Leighton et al. | 422/100 |
| 5,457,041 A | * 10/1995 | Ginaven et al. | 435/172.1 |
| 5,478,744 A | 12/1995 | Sanford | 435/285.1 |
| 5,501,893 A | 3/1996 | Laermer | 428/161 |
| 5,877,008 A | 3/1999 | Remenyik | 435/285.1 |
| 5,964,726 A | 10/1999 | Korenstein | 604/20 |
| 6,040,184 A | 3/2000 | Greener | 435/461 |
| 6,060,315 A | 5/2000 | Holcomb | 435/446 |
| 6,096,020 A | 8/2000 | Hofmann | 604/501 |
| 6,120,493 A | 9/2000 | Hofmann | 604/506 |
| 6,133,670 A | 10/2000 | Rodgers | 310/309 |
| 6,135,990 A | 10/2000 | Heller | 604/500 |
| 6,175,170 B1 | 1/2001 | Kota | 310/40 MM |
| 6,368,851 B1 | * 4/2002 | Baumann et al. | 435/285.2 |
| 6,383,813 B1 | * 5/2002 | Baxter et al. | 435/455 |
| 6,541,243 B1 | * 4/2003 | Harris et al. | 435/285.1 |

OTHER PUBLICATIONS

U.S. patent application Ser. No. 09/615,008, Rodgers, filed Jul. 11, 2000.
U.S. patent application Ser. No. 09/712,634, Galambos, filed Nov. 13, 2000.

* cited by examiner

*Primary Examiner*—David A. Redding
(74) *Attorney, Agent, or Firm*—John P. Hohimer

(57) ABSTRACT

An apparatus and method are disclosed for in vitro transformation of living cells. The apparatus, which is formed as a microelectromechanical device by surface micromachining, can be used to temporarily disrupt the cell walls or membrane of host cells one at a time so that a particular substance (e.g. a molecular tag, nucleic acid, bacteria, virus etc.) can be introduced into the cell. Disruption of the integrity of the host cells (i.e. poration) can be performed mechanically or electrically, or by both while the host cells are contained within a flow channel. Mechanical poration is possible using a moveable member which has a pointed or serrated edge and which is driven by an electrostatic actuator to abrade, impact or penetrate the host cell. Electroporation is produced by generating a relatively high electric field across the host cell when the host cell is located in the flow channel between a pair of electrodes having a voltage applied therebetween.

43 Claims, 13 Drawing Sheets

Section 4 - 4

Section 1 - 1

Section 3 - 3

APPARATUS AND METHOD FOR TRANSFORMING LIVING CELLS

CROSS REFERENCE TO RELATED INVENTIONS

This patent application is related to patent application Ser. Nos. 09/615,008, now U.S. Pat. No. 6,507,138, and 09/712,634, now U.S. Pat. No. 6,537,437, which are incorporated herein by reference.

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention generally relates to cell manipulation and transformation, and more particularly to a microelectromechanical (MEM) apparatus and method for transforming one or more living host cells by temporarily disrupting the integrity of the host cell so that particular substances of interest (e.g. molecules or macromolecules including DNA) can be introduced therein.

BACKGROUND OF THE INVENTION

Biologists often need to introduce into living host cells a wide range of substances which are normally excluded from the cell by the cell walls and outer cell membranes. One important application of cell manipulation is the introduction of genetic material into host cells for the purpose of genetic engineering. In this way, genetically-altered organisms can be produced for use in research, for synthesizing particular bioengineered proteins (e.g. insulin) or for producing crops having particular genetic features (e.g. resistance to pests). For these and other applications, particular biological stains, proteins, nucleic acids, organelles, chromosomes, nuclei, etc. can be introduced into biological cells.

Existing technologies for transporting genetic material into living cells involve uptake mechanisms, cell fusion, electroporation and microinjection. Uptake mechanisms generally involve suspensions of single cells, from which any existing cell wall materials have been removed enzymatically. Cell fusion incorporates genetic material into a cell by allowing that cell to fuse with another cell containing the genetic material of interest. Electroporation utilizes high electric fields to create pores in cells without causing permanent damage to the cells. Microinjection employs an extremely fine, drawn-out capillary tube (also termed a micropipette) which is used as a syringe needle to directly inject a biological substance an individual cell.

The present invention represents an improvement over the prior art by providing an apparatus and method that allows individual host cells to be transformed one at a time under carefully controlled circumstances, and in a controlled environment.

An advantage of the present invention is that host cells can be moved one at a time through a flow channel wherein each host cell can be transformed by temporarily disrupting the cell wall or membrane in a controlled and reproducible way to allow a particular substance of interest to enter into the cell, thereby transforming the cell.

Another advantage of the present invention is that the cell transformation can be performed without the need for any tedious and difficult manual alignment or manipulation.

A further advantage of the present invention is that the cell transformation can be accomplished using electrical or mechanical poration, or a combination of both.

These and other advantages of the present invention will become evident to those skilled in the art.

SUMMARY OF THE INVENTION

The present invention relates to an apparatus for transforming a host cell, comprising a flow channel lined with silicon nitride for containing the host cell and a surrounding fluid; and means, located at least partially within the flow channel, for temporarily disrupting the integrity of the host cell and thereby introducing a substance into the host cell for transforming the host cell. The flow channel and the cell disrupting means can be formed on a common substrate which generally comprises silicon.

The cell disrupting means can comprise either a pair of electrodes located proximate to the host cell on opposite sides of the flow channel for generating an electric field across the host cell in response to a voltage applied between the pair of electrodes, or a moveable member located on one side of the flow channel for mechanically abrading, impacting or penetrating the host cell. The electrodes and the moveable member can be pointed (e.g. with a single solid or hollow point, or a plurality of points or sharp edges arranged as corrugations or serrations facing the host cell). The moveable member is operatively connected to an electrostatic actuator formed on the substrate (e.g. through a compliant structure) to provide for movement thereof. This movement can be a single motion (e.g. for penetrating the host cell, or for moving into position to constrict the channel and abrade the host cell as the cell is urged along the constricted channel) or reciprocating motion (e.g. for repeatedly pricking or irritating the cell wall or membrane).

The flow channel preferably includes means for urging the host cell to move along the flow channel for proper location or alignment of the host cell prior to or during disruption of the cell membrane. This can be done, for example, by generating a pressure gradient in the fluid within the flow channel using an external pump, or by providing a plurality of electrodes spaced along the length of the flow channel to generate an electroosmotic or electrokinetic force for moving the fluid based on a voltage applied between the spaced electrodes.

Input and output ports can be connected to the ends of the flow channel for transferring the host cell and the fluid into and out from the channel. An optional third port can also be provided that is in fluid communication with the flow channel so that the cell-transforming substance (i.e. a biological stain, a protein, nucleic acid, antibody, organelle, chromosome, nuclei, virus, plasmid, bacteria, etc., which is of interest for use in transforming the host cell) can be introduced into the fluid, or directly into the host cell.

The present invention also relates to an apparatus for transforming a host cell that comprises a flow channel formed on a substrate for isolating the host cell from a plurality of other host cells within a fluid surrounding the host cell; and a moveable member formed on the substrate and located on one side of the flow channel for abrading, impacting or penetrating the host cell for transferring a substance into the host cell and thereby transforming the host cell. The moveable member is operatively connected to an electrostatic actuator located on the substrate for providing motion to the moveable member. This connection can be through a linkage which comprises a compliant structure that provides a stroke for the moveable member that is generally larger than the stroke provided by the electrostatic actuator. An end of the moveable member that abrades, impacts or penetrates the host cell can be pointed or serrated. An optional stationary member can be located opposite the moveable member, with the stationary member generally being pointed or serrated on a side thereof facing the host cell. In some embodiments of the present invention, the moveable and stationary members can form electrodes for applying a voltage across the host cell to further condition (e.g. by electroporation) the host cell for receiving the substance to be transferred therein.

The flow channel generally comprises polysilicon (i.e. polycrystalline silicon) and can be lined with silicon nitride for biocompatibility. The flow channel can further include a plurality of electrodes spaced along the length of the flow channel for generating a flow of the fluid therein in response to a voltage applied between the electrodes. This fluid flow can be used to urge the host cell along the flow channel and to align the host cell with the moveable member. The flow channel also generally includes input and output ports as described previously, and can further include an optional third port for admitting the substance to be transferred to the host cell into the fluid, or directly into the host cell (e.g. through a conduit formed in the moveable member).

The present invention further relates to an apparatus for transforming a host cell, that comprises a flow channel for isolating the host cell from a plurality of other host cells in a fluid, with the fluid further including a substance to be transferred into the host cell for transforming the host cell; a stationary electrode located on one side of the flow channel; and a moveable electrode located on the other side of the flow channel opposite the stationary electrode. The stationary and moveable electrodes are adapted to provide a voltage across the host cell when the host cell is positioned between the electrodes, with one or both of the electrodes generally being sharpened to provide a pointed or serrated edge facing the host cell. This voltage can generate an electric field across the host cell which conditions the host cell to receive the substance to be transferred therein.

The flow channel can be formed on a substrate (e.g. comprising silicon) by surface micromachining processes. The flow channel can be lined with silicon nitride for biocompatibility and to provide electrical insulation from the stationary and moveable electrodes which generally comprise polysilicon.

The apparatus can further comprise an electrostatic actuator formed on the substrate for providing motion to the moveable electrode. This motion can be a single-stroke or reciprocating motion that is in a direction substantially perpendicular to the flow channel (i.e. perpendicular to a direction of flow of the host cell in the fluid). This motion can further aid in the cell transformation by temporarily compromising the integrity of the cell membrane of the host cell through mechanical action such as impaction, penetration or irritation (e.g. pricking or abrasion). A linkage, which can comprise a compliant structure, is used to connect the electrostatic actuator to the moveable electrode.

Finally, the present invention relates to a method for transforming a host cell which comprises steps for immersing the host cell in a fluid and introducing the fluid and host cell into a flow channel; positioning the host cell adjacent to a moveable member extending into the flow channel through a sidewall thereof; and abrading, impacting or penetrating the host cell with the moveable member thereby temporarily disrupting the integrity of the host cell and forming a pathway for a substance of interest to enter the host cell for transforming the host cell. The method can further include a step for generating an electric field across the host cell by applying a voltage between a pair of electrodes located on opposite sides of the flow channel.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
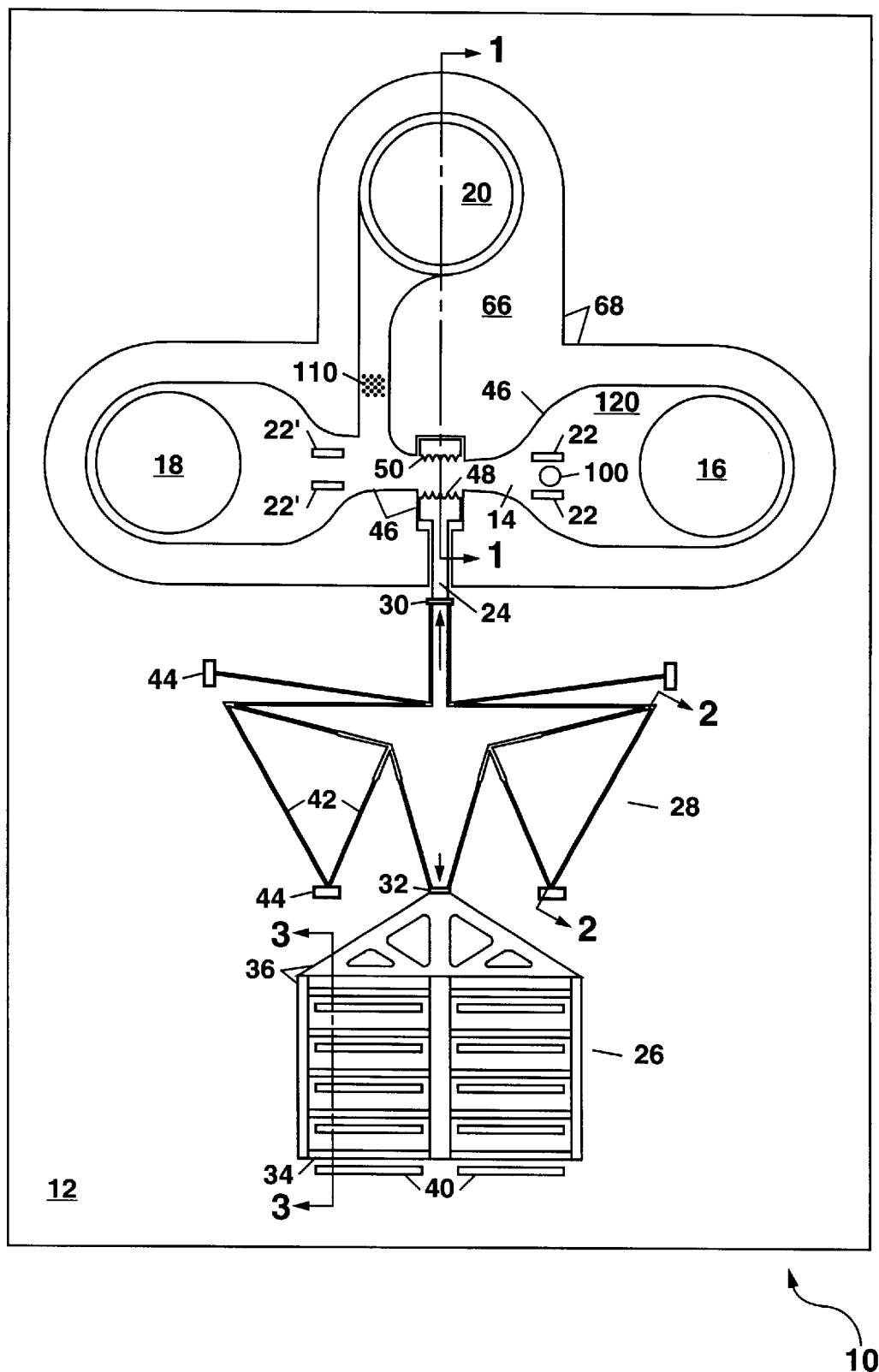
FIG. 1 shows a schematic plan view of a first embodiment of the cell transformation apparatus of the present invention.

Generally, the present invention provides an apparatus 10 and method for transforming (also termed transfecting) one or more living host cells 100 with a particular substance of interest 110 for transforming the host cells 100 without killing the cells 100. The substance 110 can be any type of molecule or macromolecule that is capable of marking the host cells 100, biochemically transforming the host cells 100, altering the host cells 100 or interacting with the host cells 100. The substance of interest can be introduced into the host cells 100 more efficiently and effectively using the apparatus 10 than would be possible via normal cell uptake mechanisms.

The present invention, which is based on single cell manipulation in vitro, can thus be used for many different applications including tagging of particular host cells 100 with biological stains 110 such as fluorescent or radiolabeled probes; or transfecting particular host cells 100 with biological particles 110 such as proteins (e.g. enzymes or hormones), nucleic acids (e.g. DNA or RNA or portions thereof), antibodies, organelles, chromosomes, nuclei, viruses, plasmids or bacteria. Thus, the present invention can be used to transfect host cells 100 with many different substances of interest 110 including ions, small molecules and macromolecules so that the host cells 100 can be differentiated from other host cells 100, so that the effect of particular substances 110 on the host cell 100 can be studied, or so that the behavior of the host cell 100 can be altered biochemically (e.g. through genetic engineering). The present invention is useful for transforming many different types of host cells 100, including bacteria, fungi, yeast, sperm, eggs, platelets, red blood cells, plant or animal cells, etc.

Referring to FIG. 1, there is shown a schematic plan view of a first embodiment of the apparatus 10 of the present invention for use in transforming one or more host cells 100. The cell transformation apparatus 10, which can be formed by surface micromachining, comprises a substrate 12 on which a flow channel 14 is formed with an input port 16 and an output port 18. The substrate 12 generally comprises silicon (e.g. a monocrystalline silicon substrate or a silicon-on-insulator substrate).

An optional third port 20 can be provided in the apparatus 10 to admit a particular substance of interest 110 into the flow channel 14 for transfection of the host cell 100. Alternately, the substance of interest 110 can be provided in a fluid 120 that is introduced into the flow channel 14 through the input port 16 and surrounds one or more host cells 100. The fluid 120 is also used to manipulate the host cells 100 and to urge the host cells 100 to move through the flow channel 14, as needed. The fluid 120 further sustains the host cells 100 while they are in the apparatus 10. The host cells 100 can be chilled prior to insertion into the apparatus 10.

The channel 14 can be necked down as shown in FIG. 1 to provide lateral dimensions (e.g. 5–50 μm) in a central portion thereof that are slightly larger (e.g. 1.5–2x) than the size of the host cells 100 so that the host cells 100 can be separated and urged to move along the channel 14 one at a time. In this way, the host cells 100 can be individually prepared with the apparatus 10 for transfection with the substance of interest 110.

In the apparatus 10 of FIG. 1, each host cell 100, after introduction into the apparatus 10 through the input port 16, can move with a flow of the fluid 120 so that the host cell 100 is initially positioned between a first pair of electrodes 22 located proximate to the necked-down central portion of the flow channel 14. The electrodes 22, which can be spaced apart by a distance that is about the size of the host cell 100 or less, can be used to electrically condition the host cell 100 by electroporation to temporarily disrupt the integrity of the host cell 100 and thereby allow the substance of interest 110 to enter into the host cell 100 for transformation thereof. A second pair of electrodes 22' is located on the opposite side of the flow channel 14 to permit further electroporation of the host cell 100. In this way, electroporation of the host cell 100 can be performed before or after mechanical poration using an elongate moveable member 24, or both.

Electroporation is a process whereby an electric field is generated across a cell to temporarily form pores (i.e. passageways) through the cell walls and membrane and into the interior of the cell. The pores can be on the order of the dimensions of the substance of interest 110, and need only remain open for a time duration from fraction of a second to a few minutes to allow the substance of interest 110 to diffuse through the cell membrane into the cytoplasm. This electrical conditioning of the host cell by electroporation can be produced by applying a pulsed voltage of, for example, 0.5–10 kilovolts/centimeter across the electrodes 22, with the voltage being provided by an external source or power supply (not shown). The external source or power supply can be computer controlled.

Electroporation is well known in the art, although it is generally not practiced in a flow channel (see e.g. U.S. Pat. Nos. 5,128,257; 5,137,817; 5,964,726; 6,040,184; 6,096,020; 6,120,493; and 6,135,990).

The fluid 120 in the flow channel 14 can be, for example, water or a buffer solution and can optionally include an osmotic stabilizer such as sucrose. The fluid 120 is generally selected to have a low electrical conductance in order to limit heating effects and/or electrolytic reactions between the electrodes 22 and the fluid 120. Electrolytic reactions can also be prevented by forming each electrode 22 from a different electrically-conductive material (e.g. doped polysilicon, a metal or metal alloy) or by providing a thin (e.g. 100–200 nanometers) electrically-insulating layer of a dielectric material (e.g. silicon nitride) that surrounds surfaces of the electrodes 22 that are exposed to the fluid 120. The electrically-insulating layer can also be optionally provided on other elements in the flow channel 14 to which voltages may be applied (e.g. to the moveable member 24 and the stationary member 50 when these members are used to form electrodes as described hereinafter with reference to FIG. 10). The flow channel 14 itself is also preferably lined with silicon nitride (e.g. 100–600 nanometers thick) for biocompatibility and electrical insulation.

In addition to or in the absence of their use for electroporation, the electrodes 22 and 22' can also be used to produce an electrokinetic or electroosmotic force in the fluid 120 to manipulate the host cell 100 as needed and to urge the host cell 100 to move along the flow channel 14 towards the exit port 18. This can be done by reconfiguring the connections to the electrodes 22 and 22' to provide a voltage from the same or a different external source or power supply directly between the electrodes 22 and 22' to generate an electric field along the length of the flow channel 14. In this way, the electrodes 22 and 22' can be used to form an electrokinetic or electroosmotic pump within the flow channel 14 so that no external pump need be used to position the host cell 100 in the necked-down central portion of the flow channel 14. This also has the advantage that the polarity of the applied voltage can be reversed, if needed, to move the host cell 100 in the opposite direction of normal fluid flow in the channel 14 so that the host cell 100 can be precisely manipulated and positioned between a moveable member 24 and a stationary member 50.

In the first embodiment of the apparatus 10 shown in FIG. 1, the integrity of the host cell 100 can also be disrupted mechanically using the moveable member 24 which can be actuated to move back and forth in the flow channel 14. The moveable member 24, which can be formed on the substrate 12 by surface micromachining using the same series of process steps described hereinafter for forming the remainder of the apparatus 10, is located on one side of the necked-down central portion of the flow channel 14. In operation, the moveable member 24 can be used to abrade, impact or penetrate the membrane of the host cell 100 in order to temporarily disrupt its integrity (e.g. by mechanical poration) to form one or more pores or pathways for the substance of interest 110 to enter into the host cell 100 to transform it. The provision of both mechanical and electrical cell disruption means in the flow channel 14 provides increased flexibility to allow transformation of many different types of host cells 100 since these disruption means can be used singly or in combination. Additionally, the combination of mechanical and electrical poration is expected to increase the yield for transformation of host cells 100 compared to the use of either mechanical poration or electrical poration alone.

In FIG. 1, the moveable member 24 can be actuated using an electrostatic actuator 26 which is also formed on the substrate 12 by conventional surface micromachining, and which is operatively connected to the moveable member 24. When a long-stroke electrostatic actuator (e.g. a conventional electrostatic comb actuator having a stroke of about 10 μm) is used, the electrostatic actuator can be directly connected to the moveable member 24. When a short-stroke electrostatic actuator 26 (e.g. with a displacement stroke of generally $\leq 5$ μm) is used as shown in FIG. 1, some multiplication of the displacement stroke may be necessary. This displacement multiplication can be provided by a surface micromachined compliant structure 28. The compliant structure 28 provides a forward and backward stroke for the moveable member 24 that is larger than the stroke provided by the electrostatic actuator 26. This multiplication in displacement is accompanied by a corresponding reduction in an actuation force provided to the moveable member 24 at its connection to an output side 30 of the compliant member 28 as compared to the actuation force provided to an input side 32 of the compliant member 28 by the electrostatic actuator 26. The provision of a short-stroke electrostatic actuator 26 operating in combination with the displacement multiplier 28 generally takes up less space on the substrate 12 than the long-stroke electrostatic actuator while providing about the same actuation force to the moveable member 24.

In FIG. 1, operation of the short-stroke electrostatic actuator 26 with an actuation voltage (e.g. $\leq 40$ volts) provided by a power supply or source (not shown) which can be computer controlled generates a displacement of, for example, 2–3 μm at the input side 32 of the compliant structure 28 in a direction that is substantially perpendicular to the channel 14. This input displacement arises from an electrostatic force of attraction produced between a plurality of moveable capacitive plates 34 (or alternately moveable electrostatic combs), which are ganged together and attached to a frame 36 which, in turn, is suspended above the substrate 12 by springs 38 which are not visible in FIG. 1 since they underlie the frame 36 (see FIG. 5), and a plurality of stationary capacitive plates 40 (or alternately stationary electrostatic combs) which are fixed on the substrate 12. The springs 38 act to return the moveable capacitive plates 34 to their initial rest position upon removal of the actuation voltage. Both unidirectional and bidirectional electrostatic actuators 26 can be used in the apparatus 10 of the present invention. Short-stroke capacitive plate electrostatic actuators and electrostatic comb actuators are disclosed, for example, in U.S. Pat. Nos. 6,133,670 and 6,175,170 which are incorporated herein by reference.

The compliant structure 28 comprises a plurality of flexible beams 42 formed by surface micromachining from a plurality of stacked layers of deposited and patterned polycrystalline silicon (also termed polysilicon), silicon nitride or both. These beams 42 are supported above the substrate 12 by a plurality of support posts 44 with certain of the beams 42 being attached to each other and to the input and output sides, 32 and 30, respectively as shown in FIG. 1 (see also FIG. 7). In the embodiment of the apparatus 10 in FIG. 1, the compliant structure 28 converts the input displacement of the electrostatic actuator 26 (shown by the small arrow in FIG. 1) into a multiplied output displacement (shown by the large arrow in FIG. 1). The compliant structure 28 can be designed to provide the multiplied output displacement in a direction opposite the input displacement from the electrostatic actuator 26 as shown in FIG. 1, or alternately in the same direction as the input displacement. The multiplication in displacement is determined by the exact design of the compliant structure 28, and can be in the range of about 5–60 times the displacement provided by the electrostatic actuator 26. Further details about surface-micromachined compliant structures can be found in U.S. Pat. No. 6,175,170 which is incorporated herein by reference.

In FIG. 1, the compliant structure 28 couples mechanical power from the electrostatic actuator 26 into the moveable member 24 to enable the member 24 to be moved into or out of the channel 14 as needed to mechanically abrade, impact or penetrate the host cell 100. Close tolerances (e.g. 1–2 μm) between the moveable member 24 and inner sidewalls 46 of the flow channel 14 and top and bottom surfaces of the channel 14 are sufficient to prevent escape of the fluid 120 from the channel 14 upon movement of the member 24. Additionally, movement of the member 24 is limited to a predetermined range so that no fluid 120 is trapped behind an enlarged portion of the moveable member 24 containing a pointed or serrated end 48 and the inner sidewall 46. Finally, if needed, an anti-stiction coating as known to the art can be liquid or vapor deposited on the moveable member 24 and inner sidewalls 46 of the flow channel 14 after removal of the sacrificial material 58 to prevent seizing or sticking of the moveable member 24 to the sidewalls 46 and top and bottom of the flow channel 14 and also to prevent stiction (i.e. adhesion) of other elements of the apparatus 10 (e.g. to the substrate 12).

In one mode of operation of the apparatus 10 of FIG. 1, mechanical abrasion of the host cell 100 can be generated by moving the moveable member 24 into the channel 14 to narrow the width of the channel 14 at this point to being smaller than the width of the host cell 100. As the host cell 100 is urged to move through this narrowed portion of the channel due to a pressure gradient in the fluid 120 along the length of the channel 14, the host cell 100 can be abraded by rubbing against the pointed or serrated end 48 of the moveable member 24. The pressure gradient in the fluid 120 can be generated by an external pump (not shown), or alternately by an internal electrokinetic or electroosmotic pump formed by applying a voltage across the electrodes 22 and 22'. As shown in FIG. 1, an optional stationary member 50 can be provided on the opposite side of the channel 14 with a pointed or serrated edge to provide further abrasion on the other side of the host cell 100 to allow increased porosity for the substance of interest 110 to enter into and transform the cell 100. This mechanical abrasion of the host cell 100 can be used with or without electroporation as previously described.

In another mode of operation of the apparatus 10 of FIG. 1, one or more mechanical impulses can be provided by the moveable member 24 to impact the host cell 100 and thereby disrupt the integrity of the cell wall or membrane. This can be done by providing a cyclic actuation voltage (e.g. a square-wave voltage) to the electrostatic actuator 26. The motion of the moveable member 24 can be reciprocating (i.e. forward and backward) for a predetermined number of cycles as needed to condition the host cell 100 for admitting the substance of interest 110. A computer or signal generator can be used to generate and control the cyclic actuation voltage.

In this mode of operation, the host cell 100 is urged along the flow channel 14 until the host cell 100 is located in the path of the moveable member 24 which is initially retracted into a recess in the inner sidewall 46 as shown in FIG. 1. With the host cell 100 in position, the cyclic actuation voltage can be provided to the electrostatic actuator 26 to drive the moveable member 24 forward into the flow channel 14 to impact the host cell 100. A lowering or removal of the actuation voltage allows the springs 38 in the electrostatic actuator 26 to return the actuator 26 and moveable member 24 to their initial rest positions in preparation for additional impaction of the host cell 100 when the actuation voltage is increased or reapplied.

With each impact, a pointed or serrated end 48 of the moveable member 24 pricks, abrades, penetrates or otherwise temporarily disrupts the integrity of the host cell 100, thereby allowing the substance of interest 110 to enter the host cell 100 through pores formed in the cell membrane by the impacts. These impacts can also directly force the substance of interest 110 into the host cell 100 (e.g. when the substance 110 is located on the surface of the cell 100, located on a pointed end of the member 24 which penetrates the cell 100, or trapped between the cell 100 and the member 24). The exact number of impacts required for transformation of the host cell 100 will depend upon the type of host cell 100 being processed with the apparatus 10 and the particular substance of interest 110 that is to be transfected into the host cell 100, and can be determined from practice of the present invention. Additional pricking, abrasion, penetration or disruption of the host cell 100 can be provided by the optional stationary member 50 which can have a pointed or serrated sidewall facing the host cell 100 as shown in FIG. 1.

After conditioning of the host cell 100 with the moveable member 24, the host cell 100 can remain in place for a period of time to allow the substance of interest 110 to enter into the cell 100. Alternately, the host cell 100 can be moved along the flow channel 14 toward an intersection with a secondary channel connected to the third port 20. At this point, a substance of interest 110 introduced into the flow channel 14 via the third port 20 can contact the host cell 100 and enter therein. Electroporation provided by the first pair of electrodes 22 and/or the second pair of electrodes 22' can also be used to prepare the host cell 100 for receiving the substance of interest 110. Once transformation of the host cell 100 is completed, the host cell 100 can be removed from the apparatus 10 through exit port 18.

The input and exit ports, 16 and 18, and the third port 20 can be etched completely through the substrate 12 so that fluid connections (e.g. with microcapillary tubing attached to the backside of the substrate 12 using an epoxy or elastomeric adhesive) can be made to the apparatus 10 from a backside thereof. Etching the various ports 16, 18 and 20 can be performed using a deep reactive ion etching process which combines multiple anisotropic etching steps with steps for simultaneously depositing an isotropic polymer/inhibitor to minimize lateral etching. Such a deep etching process is disclosed in U.S. Pat. No. 5,501,893 to Laermer et al, which is incorporated herein by reference.

In some embodiments of the present invention, the host cell 100 after transformation thereof can be directed to other devices formed on the substrate 12 and connected to the flow channel 14 for further processing, cell sorting, incubation or analysis.

The apparatus 10 of FIG. 1 can be fabricated using a series of surface micromachining process steps as described hereinafter with reference to FIGS. 2A–2L which show schematic cross-section views of the apparatus 10 along the section line 1—1 in FIG. 1. It will be understood by those skilled in the art that the same series of process steps described with reference to FIGS. 2A–2L can be used to build up the structure of the electrostatic actuator 26 and the compliant structure 28 layer by layer.

In FIGS. 2A–2L, only selected process steps are illustrated as needed to understand the present invention. Those skilled in the art will understand that surface micromachining involves the deposition and patterning of a plurality of layers of different materials including polysilicon, silicon dioxide, silicon nitride, silicate glass, metals and metal alloys. The term "patterning" as used herein refers to a sequence of well-known integrated circuit (IC) processing steps including applying a photoresist to the substrate 12 or to a layer deposited thereon, pre-baking the photoresist, aligning the substrate 12 to a photomask (also termed a reticle), exposing the photoresist through the photomask, developing the photoresist, baking the wafer, etching away the surfaces not protected by the photoresist, and stripping the protected areas of the photoresist so that further processing can take place. The term "patterning" can further include the formation of a hard mask (e.g. comprising about 500 nanometers of a silicate glass deposited from the decomposition of tetraethylortho silicate, also termed TEOS, by low-pressure chemical vapor deposition at about 750° C. and densified by a high temperature processing) overlying a polysilicon or sacrificial material layer in preparation for defining features into the layer by etching.

Figure 2A:
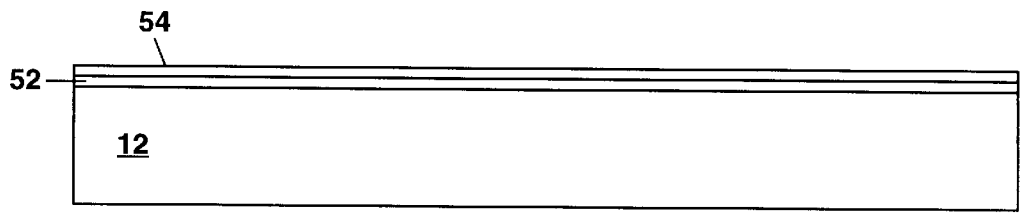
FIGS. 2A–2L schematically illustrate cross-section views of the first embodiment of the present invention along the section line 1—1 in FIG. 1 during fabrication by a series of surface-micromachining process steps.

In FIG. 2A, a substrate 12 is provided to begin the process of fabricating the apparatus 10 by surface micromachining. The substrate 12 will generally comprise silicon (e.g. a silicon or silicon-on-oxide wafer or portion thereof) although other types of substrates 12 can be used (e.g. comprising glass, quartz, fused silica, ceramic and metal). The substrate can be electrically conducting or electrically insulating since electrical connections to the apparatus 10 are made to portions thereof (e.g. a Poly-0 layer) which are electrically isolated from the substrate 12.

The substrate 12 can be initially prepared by forming a layer of thermal oxide 52 (e.g. about 0.6 $\mu$m thick) on exposed surfaces of the substrate 12. This can be done using a conventional wet oxidation process at an elevated temperature (e.g. 1050° C. for about 1.5 hours). A layer of low-stress silicon nitride 54 (e.g. 0.8 $\mu$m thick) can then be deposited over the thermal oxide layer using low-pressure chemical vapor deposition (LPCVD) at about 850° C. LPCVD is a conformal deposition process which deposits the silicon nitride 54 or other deposited material conformally over exposed surfaces of the substrate 12.

The layers 52 and 54 of thermal oxide and silicon nitride, respectively, provide electrical isolation from the substrate 12 for a subsequently-deposited layer (termed Poly-0) of polysilicon 56 which is patterned by photolithographic definition and etching (e.g. reactive ion etching) to form wiring 80 for making electrical connections from the electrodes 22 and 22' and the electrostatic actuator 26 to associated bond pads 92 on the substrate 12 (see FIGS. 5 and 10). This layer of the polysilicon 56, which can be deposited to a thickness of 0.3 $\mu$m using LPCVD at about 580° C., is also used to form ground planes as needed (e.g. underneath the electrostatic actuator 26 and the compliant structure 28). Phosphorous doping can be used to make the polysilicon 56 electrically conductive as needed. After deposition and patterning, the Poly-0 layer and other subsequently-deposited layers of the polysilicon 56 can be annealed at a high temperature (e.g. at about 1100° C. for three hours) to reduce any stress therein.

Figure 2B:
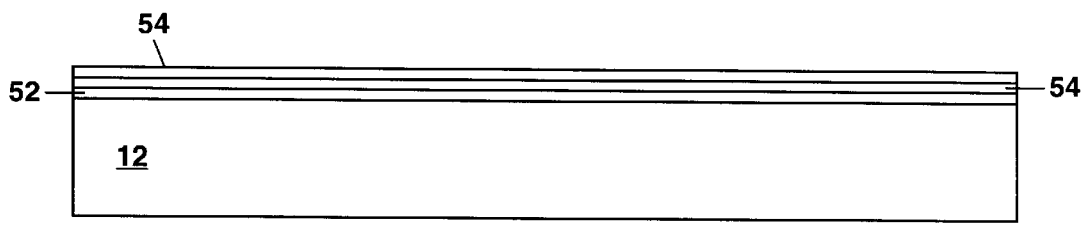

In FIG. 2B, another layer of the silicon nitride 54 is blanket deposited over the substrate 12 by LPCVD to a layer thickness in the range of 0.1–2 $\mu$m, and preferably about 0.3 $\mu$m. The silicon nitride 54 is then patterned to provide openings down to the underlying polysilicon 56 at locations where the electrical wiring 80 must be connected to electrically-active elements of the apparatus 10 (e.g. at the locations of the electrodes, 22 and 22', and at the locations of the moveable and stationary capacitive plates, 34 and 40). This layer of the silicon nitride 54 is also used to line the bottom surface of the flow channel 14 for biocompatibility and electrical insulation.

Figure 2C:
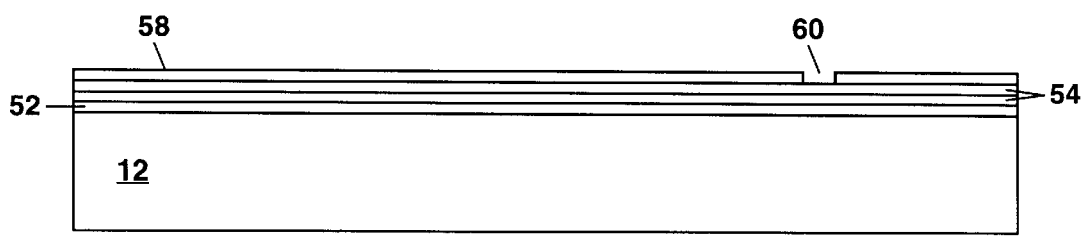

In FIG. 2C, a first layer of a removable sacrificial material 58 is deposited over the substrate 12 and patterned to provide a plurality of shaped openings 60 wherein a subsequent layer of the polysilicon 56 (termed Poly-1) is to be deposited and patterned (see FIG. 2D) to build up the apparatus 10 layer by layer. This patterning step can utilize a hard mask (e.g. comprising TEOS) formed over the sacrificial material 58 for use in etching the openings 60 by reactive ion etching. The openings 60 can extend down through the sacrificial material 58 as needed to permit elements of the apparatus 10 formed from the polysilicon 56 to be attached to the substrate 12. Other elements (e.g. the moveable member 24) are spaced above the substrate 12 by a distance less than or equal to the thickness of this first layer of the sacrificial material 58. A plurality of dimples 62 (see FIG. 3) can be etched partway through the layer of the sacrificial material 58 in FIG. 2C to limit contact between moveable members (e.g. the compliant structure 28) and the substrate 12.

The sacrificial material 58, which can comprise silicon dioxide or a silicate glass such as TEOS, can be deposited over the substrate 12 in multiple layers to provide an overall thickness in the range of 1–10 $\mu$m or more. The exact thickness and number of layers of the sacrificial material 58 which must be deposited will depend on the height of the flow channel 14 to be formed which, in turn, depends upon the type of host cells 100 to be processed with the apparatus 10. Each deposited layer of the sacrificial material 58 can be, for example, about 0.5–2 $\mu$m thick.

Figure 2D:
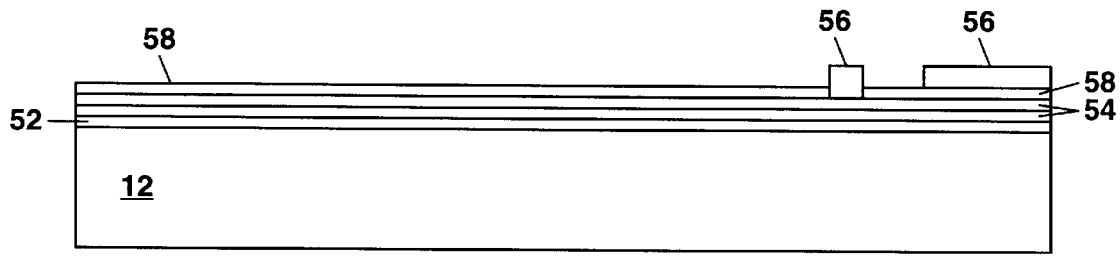

In FIG. 2D, another layer (termed Poly-1) of the polysilicon 56 is deposited over the substrate 12 to a layer thickness of, for example, 1–2 $\mu$m. This polysilicon layer is then patterned to begin to build up elements of the apparatus 10 including the electrodes 22 and 22'; the moveable and stationary members, 24 and 50; the beams 42 and support posts 44 of the compliant structure 28; and the capacitive plates 34 and 40 and frame 36 of the electrostatic actuator 26.

Figure 2E:
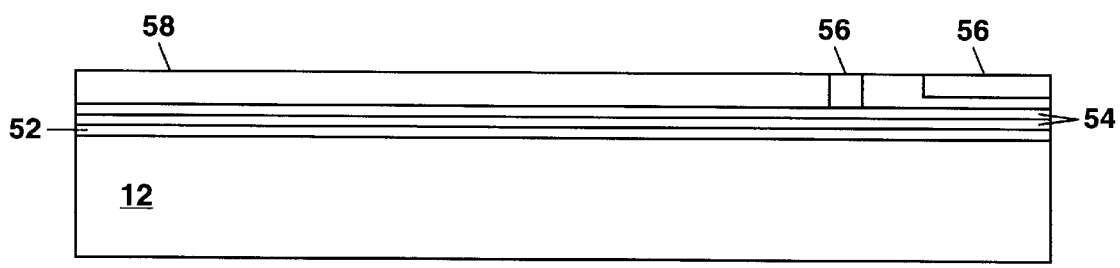

In FIG. 2E, another layer of the sacrificial material 58 is deposited over the substrate 12. Each layer of the sacrificial material 58 and the polysilicon 56 can be planarized by chemical-mechanical polishing, as needed, to reduce variations in the topography of the apparatus 10 as it is being formed. Chemical-mechanical polishing as applied to surface micromachining is disclosed in U.S. Pat. No. 5,804,084 which is incorporated herein by reference.

Figure 2F:
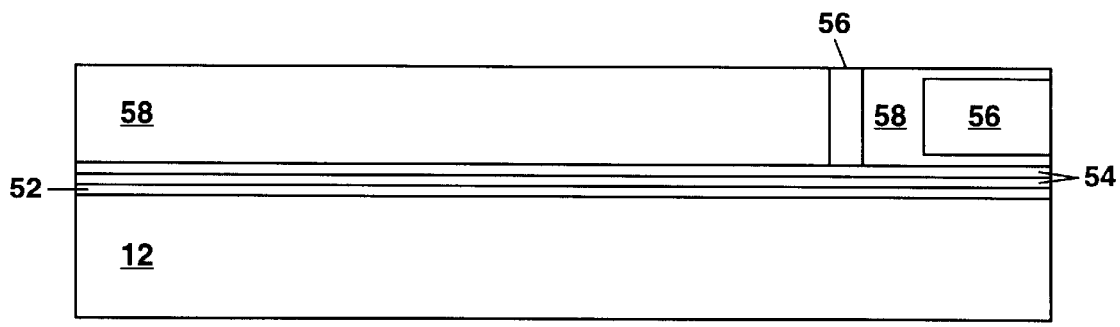

In FIG. 2F, additional layers of the polysilicon 56 and the sacrificial material 58 are alternately deposited and patterned to further build up the structure of the apparatus 10. The exact number of layers of the polysilicon 56 and the sacrificial material 58 will depend upon the size of the host cells 100 being processed with the apparatus 10. For certain embodiments of the present invention, a total of five layers of the polysilicon 56 can be used to provide a channel height of about 6–10 $\mu$m.

Figure 2G:
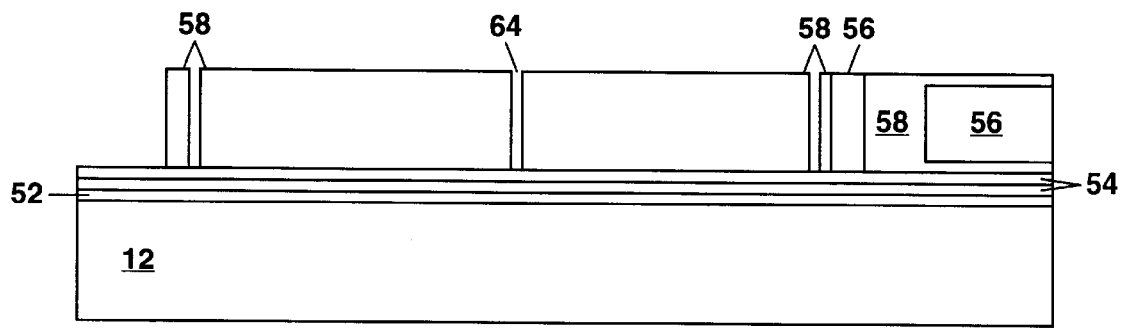
Figure 2H:
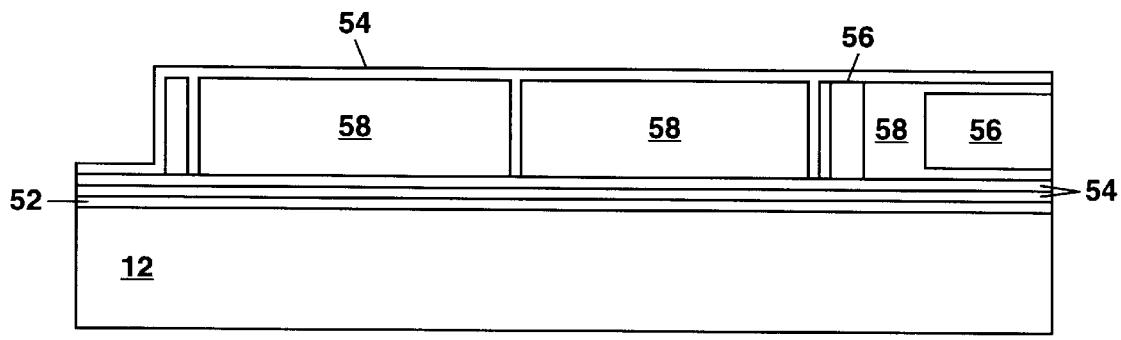

In FIG. 2G, trenches 64 are etched down through the sacrificial material 58 to define the locations of the inner sidewalls 46 to be formed to line the flow channel 14 and the ports 16, 18 and 20. In FIG. 2H silicon nitride 54 is deposited by LPCVD to fill in the trenches 64 and blanket the sacrificial material 58. Although not shown in FIG. 2H, the silicon nitride 54 can also be used to line surfaces of the moveable member 24 and the stationary member 50, especially those surfaces which come into contact with the host cell 100. This layer of the silicon nitride 54 forms an inner lining of the channel 14 in combination with an underlying layer of the silicon nitride 54 formed in the step described previously with reference to FIG. 2B. The thickness of each layer of the silicon nitride 54 can be about the same (e.g. 0.8 $\mu$m thick).

In FIG. 1, certain portions 66 of the sacrificial material 58 located between the inner sidewalls 46 and outer sidewalls 68 are completely encapsulated by the various layers of the silicon nitride 54 so that these portions 66 need not be removed during a selective etching step that removes the sacrificial material 58 from the flow channel 14, and from encapsulating the moveable member 24, the compliant structure 28 and the electrostatic actuator 26. These encapsulated portions 66 are retained to define the structure of the flow channel 14 and the inner and outer sidewalls, 46 and 68, thereof.

Figure 2I:
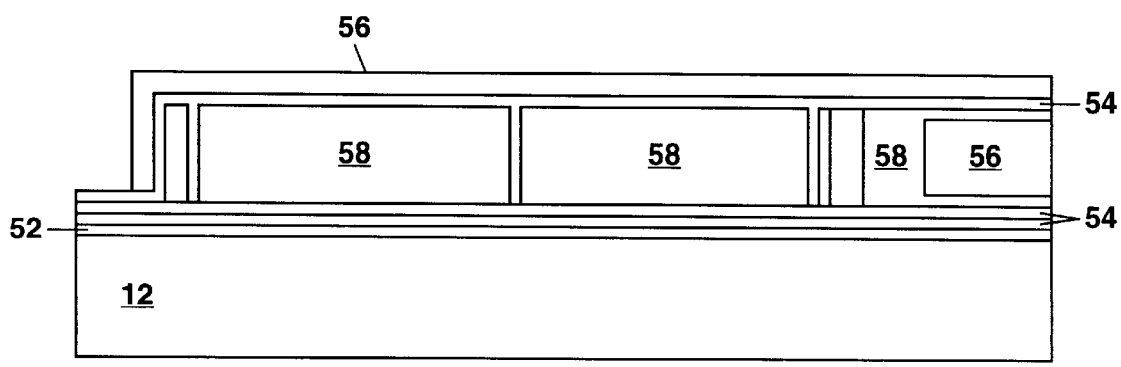

In FIG. 2I, another layer of the polysilicon 56 about 1–2 $\mu$m thick can be deposited over the substrate 12 to strengthen the flow channel 14. Additionally, this layer of the polysilicon 56 can be used to optionally form an electrode overlying the channel 14 which can be used in combination with another electrode formed in the Poly-0 layer and underlying the channel. These electrodes (not shown), which can be located about the flow channel 14 proximate to the moveable member 24 can be used with an applied voltage to provide a vertically-oriented electric field for electroporation of the host cell 100.

Figure 2J:
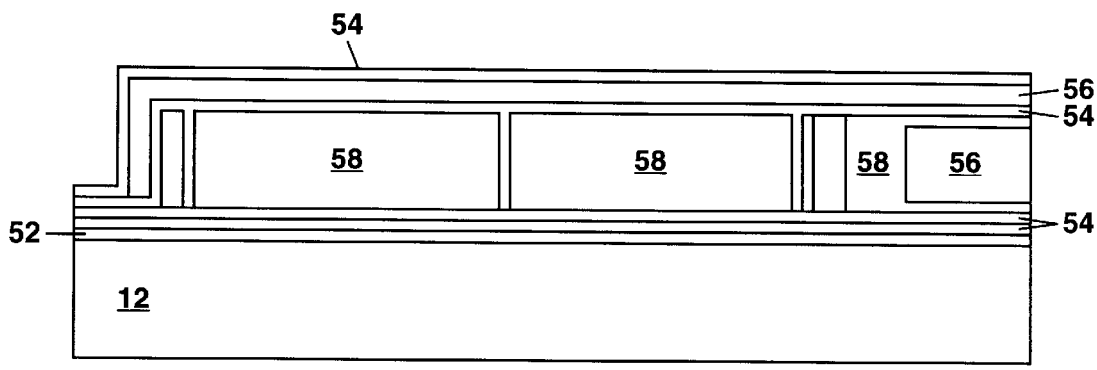

In FIG. 2J, the strengthening layer of the polysilicon 56 can be optionally overcoated with yet another layer of silicon nitride 54. If needed, yet another layer of the polysilicon 56 (not shown) can be added depending upon the pressure or pressure gradient which will exist in the flow channel 14 during operation of the device 10.

Figure 2K:
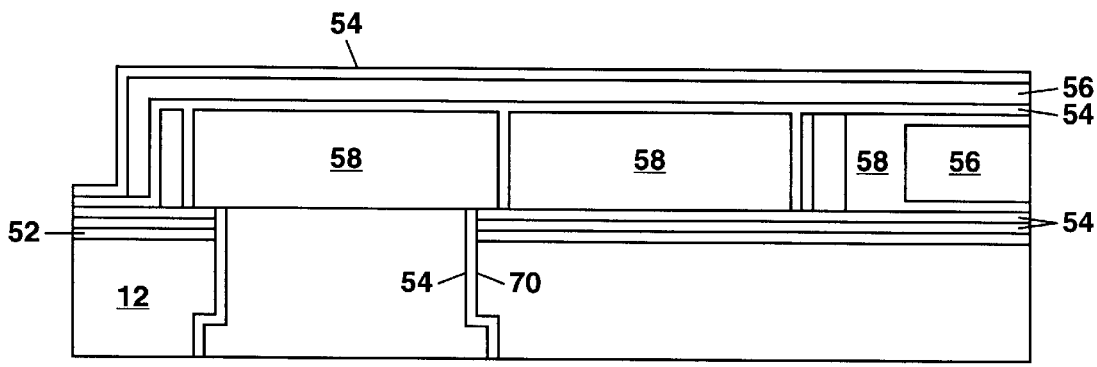
Figure 2L:
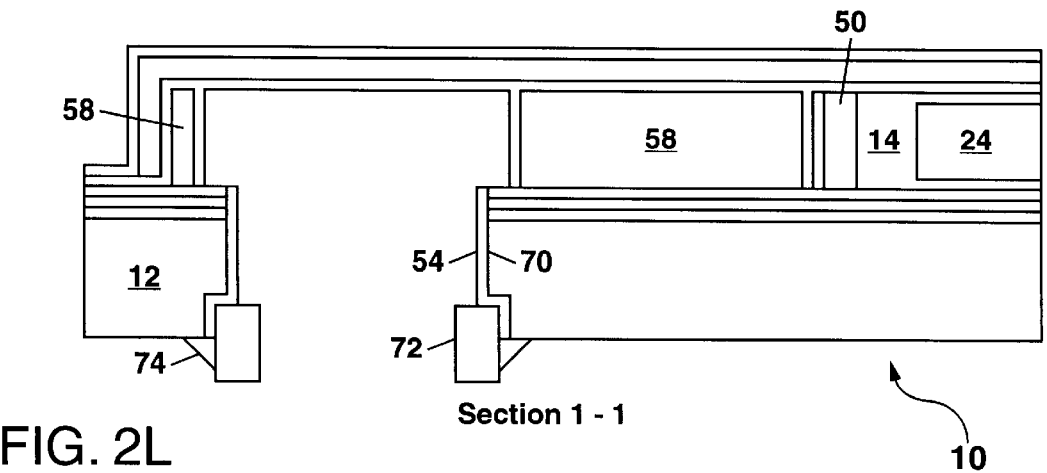

To complete formation of the apparatus 10, the sacrificial material 58 must be removed partially or entirely from the flow channel 14, the moveable member 24, the compliant structure 28 and the electrostatic actuator 26. This can be done either before or after formation of the various ports 16, 18 and 20. FIGS. 2K and 2L illustrate formation of the ports 16, 18 and 20 prior to removal of the sacrificial material 58.

In FIG. 2K, the ports 16, 18 and 20 can be formed by etching holes 70 through the backside of the substrate 12 using a deep reactive ion etching process which combines multiple anisotropic etching steps with steps for simultaneously depositing an isotropic polymer/inhibitor to minimize lateral etching. Such a deep etching process is disclosed, for example, in U.S. Pat. No. 5,501,893 to Laermer et al, which is incorporated herein by reference. A conventional anisotropic reactive ion etching step can then be used, if needed, to etch through any remaining material layers (e.g. comprising silicon dioxide or silicon nitride) separating the substrate 12 from the sacrificial material 58 in the region wherein the ports 16, 18 and 20 are being formed. The etched holes 70 can then be lined with a layer of LPCVD silicon nitride 54 (e.g. 0.8 thick). These holes 70 extending through the substrate 12 form the ports 16, 18 and 20, can be optionally stepped as shown in FIG. 2K or tapered at the backside of the substrate 12 to facilitate the insertion of microcapillary tubing 72 which can be secured with an adhesive 74. This allows fluid connections to be made to the apparatus 10 for introducing the host cells 100, the substance of interest 110 and the fluid 120 into the apparatus 10, and for removing these elements from the apparatus 10 after transformation of the host cells 100.

In FIG. 2L, the sacrificial material 58 can be removed from the flow channel 14 and from surrounding the moveable member 24, the compliant structure 28 and the electrostatic actuator 26 using a selective etchant comprising hydrofluoric acid (HF) in a liquid solution or vapor form. The etching step generally requires several hours or over night to completely remove the sacrificial material 58 accessible to the selective etchant. No substantial etching of the silicon nitride 54, polysilicon 56, metals such as tungsten, gold or platinum, or the substrate 12 occurs during this etching step.

Access of the selective etchant to the flow channel 14 can be provided through the holes 70. To access difficult-to-reach regions of the apparatus 10 wherein sacrificial material 58 must be removed, a plurality of micron-sized etch access holes can be etched downward through any material layers overlying the sacrificial material 58, if needed. After removal of the sacrificial material 58 by the selective etchant, these etch access holes can be optionally plugged with LPCVD-deposited silicon nitride.

FIG. 2L shows a schematic cross-section view along the section line 1—1 in FIG. 1 for the completed device 10 with microcapillary tubing 72 attached.

Figure 3:
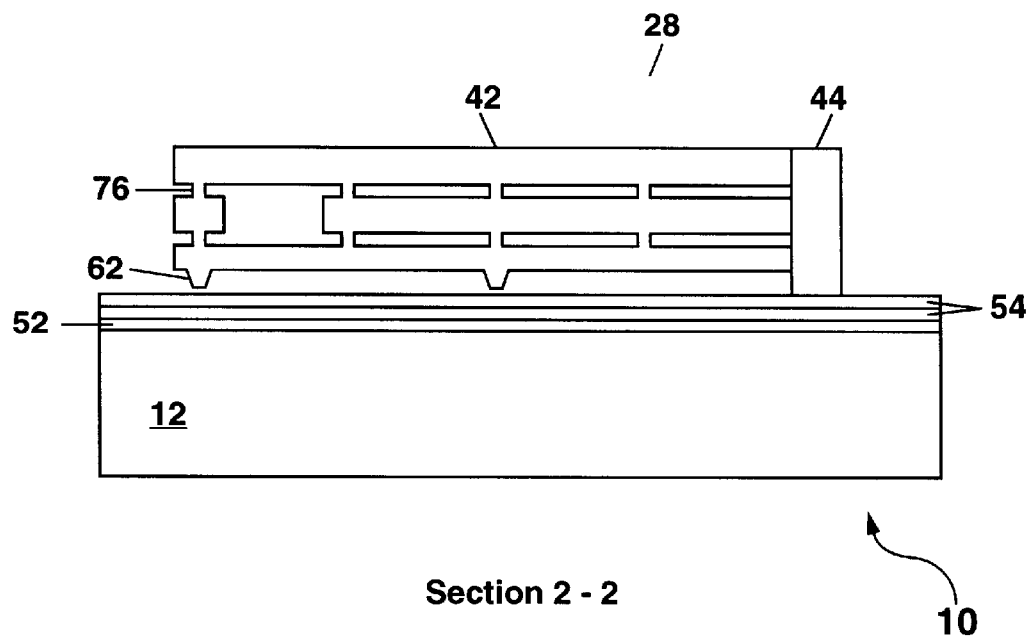
FIG. 3 schematically illustrates a cross-section view of the compliant structure along the section line 2—2 in FIG. 1.

The same series of process steps described with reference to FIGS. 2A–2L are also used to fabricate the compliant structure 28 and the electrostatic actuator 26 by the same surface-micromachining process steps. FIG. 3 shows a schematic cross-section view of the compliant structure 28 along the section line 2—2 in FIG. 1. In FIG. 3, the structure of the compliant structure 28 is built up from the polysilicon 56 layer by layer using the series of process steps described previously with reference to FIGS. 2A–2L. Portions of the compliant structure 28 can be optionally formed from deposited and patterned layers of the silicon nitride 54 using the same steps used to deposit and pattern the silicon nitride 54 in and about the flow channel 14.

In FIG. 3, the structure of the compliant structure 28 comprises a plurality of flexible beams 42 which are each formed from multiple stacked layers of the polysilicon 56 (e.g. Poly-1, Poly-2 and Poly-3 layers) interconnected by polysilicon vias 76. This stacked arrangement increases the structural rigidity of the beams 42, especially to prevent movement out of the plane of the substrate 12. Each beam 42 can have a width of 1–10 µm and preferably about 1–2 µm, a height on the order of 10 µm or less, and a length of generally 50–200 µm. An overall area of the compliant structure 28 is generally a fraction of a millimeter on a side (e.g. 212 µm wide ×240 µm high). Compliance of the structure 28 is preferably distributed throughout the entire structure 28, thereby forming a flexible mechanism that can multiply the displacement provided by the electrostatic actuator 26 without any rubbing joints. One or more dimples 62 can be formed in the lowest layer (i.e. Poly-1) of the beams 42 as shown in FIGS. 3 and 4 to allow the beams 42 to flex and move over the surface of the substrate 12 with reduced surface friction.

Figure 4:
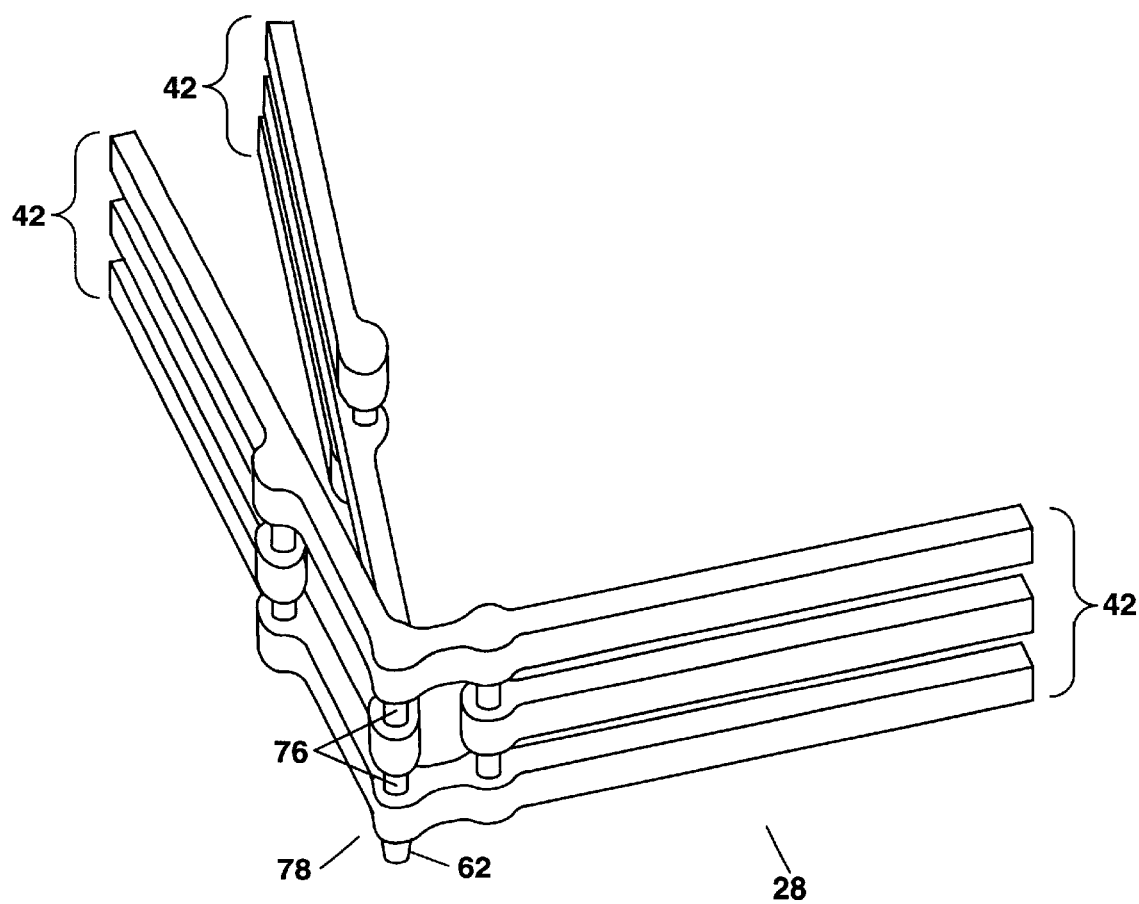
FIG. 4 shows a schematic perspective view of a portion of the compliant structure to illustrate the structure and connection of a plurality of beams therein.

FIG. 4 schematically illustrates in perspective view how a compliant joint 78 can be formed at each intersection of three of the beams 42 in FIG. 1. The joints 78 are formed by patterning the different polysilicon layers differently so that a central beam 42 can be inserted into an intersection of two outer beams 42. The three beams 42 are interconnected using vias 76 formed in intervening layers of the sacrificial material 58 which has been removed in the released structure 28 of FIG. 4. Each joint 78 is preferably formed with a dimple 62 underneath to reduce surface friction upon rubbing over the surface of the substrate 12.

Fabrication of the electrostatic actuator 26 is also performed simultaneously with fabrication of the compliant structure 28, the moveable member 24 and the flow channel 14 using the series of process steps described previously with reference to FIGS. 2A–2L.

Figure 5:
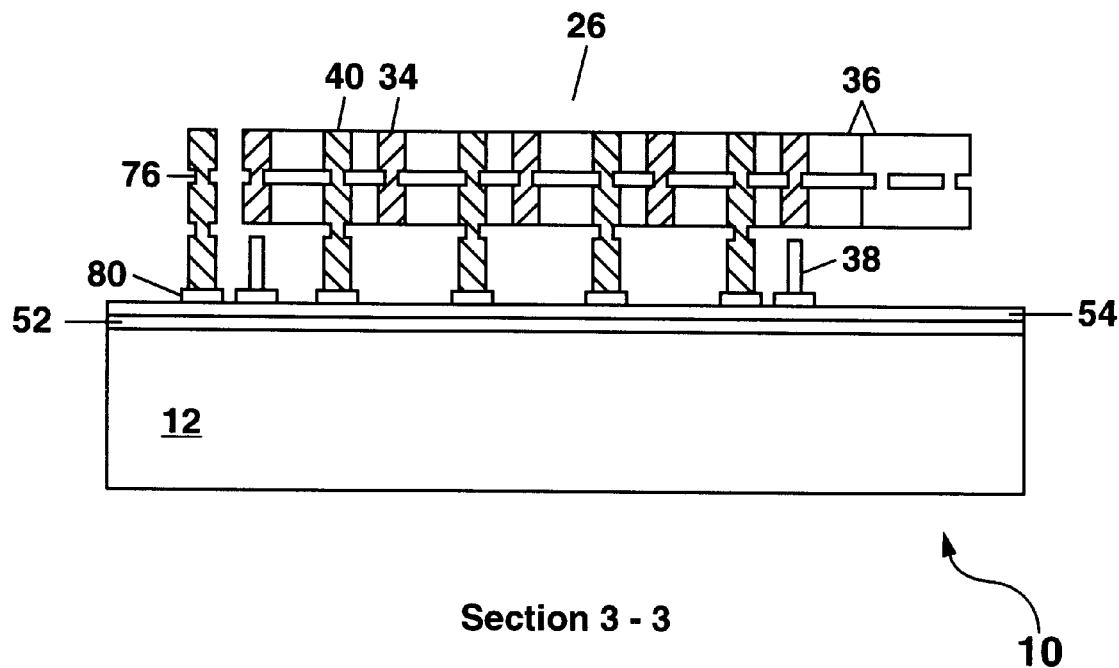
FIG. 5 schematically illustrates a cross-section view of the electrostatic actuator along the section line 3—3 in FIG. 1.

FIG. 5 shows a schematic cross-section of the capacitive plate electrostatic actuator 26 along the section line 3—3 in FIG. 1. In FIG. 5, electrical wiring 80 to the stationary capacitive plates 40 is formed by patterning a first-deposited layer of polysilicon 56 (i.e. Poly-0). Electrical connections to the moveable capacitive plates 34, which are preferably held at ground electrical potential, is made through the springs 38 which are anchored at one end thereof to the substrate 12 or to electrical wiring 80 formed on the substrate 12 and at the other end thereof to the frame 36.

The moveable and stationary capacitive plates, 34 and 40, the springs 38 and the frame 36 are built up from the a plurality of stacked layers of the polysilicon 56, with vias 76 interconnecting the various layers. The moveable capacitive plates 34 are rigidly supported by the frame 36 so that, when the actuation voltage is applied between the moveable and stationary capacitive plates, 34 and 40, the moveable capacitive plates 34 are urged towards the stationary capacitive plates 40, thereby moving the frame 36 and generating a displacement for moving the moveable member 24.

Electrical short-circuiting between the moveable and stationary capacitive plates, 34 and 40, can be prevented by locating one or more stops (not shown) therebetween. Such stops, which are formed of an electrically insulating material such as the silicon nitride 54, can be about 1 µm thick or less and formed on a portion of a sidewall of the stationary capacitive plates 40 that could otherwise come into contact with the moveable capacitive plates 34.

Figure 6:
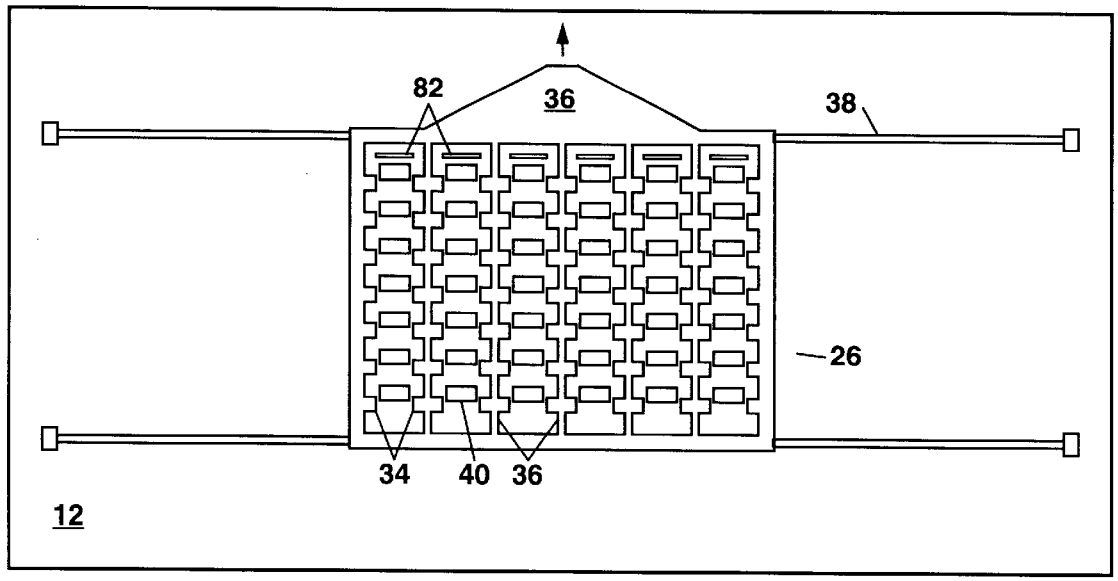
FIG. 6 shows a schematic plan view of an alternative type of electrostatic actuator that can be used in the apparatus of FIG. 1.

Another way of preventing electrical short-circuiting of the capacitive plates 34 and 40 is to form rows of the stationary capacitive plates 40 located between other rows of the moveable capacitive plates 34 as shown in FIG. 6. This type of electrostatic actuator 26, which has a rigid structure to prevent lateral motion while providing for motion in the direction shown by the arrow, can be formed using the same series of surface micromachining process steps described previously with reference to FIGS. 2A–2L. A plurality of electrostatic shields 82 formed from the deposited and patterned polysilicon 56 can be used to reduce or eliminate an unwanted electrostatic force that acts oppositely to the electrostatic force generated between the moveable and stationary capacitive plates 36 and 40.

Figure 7:
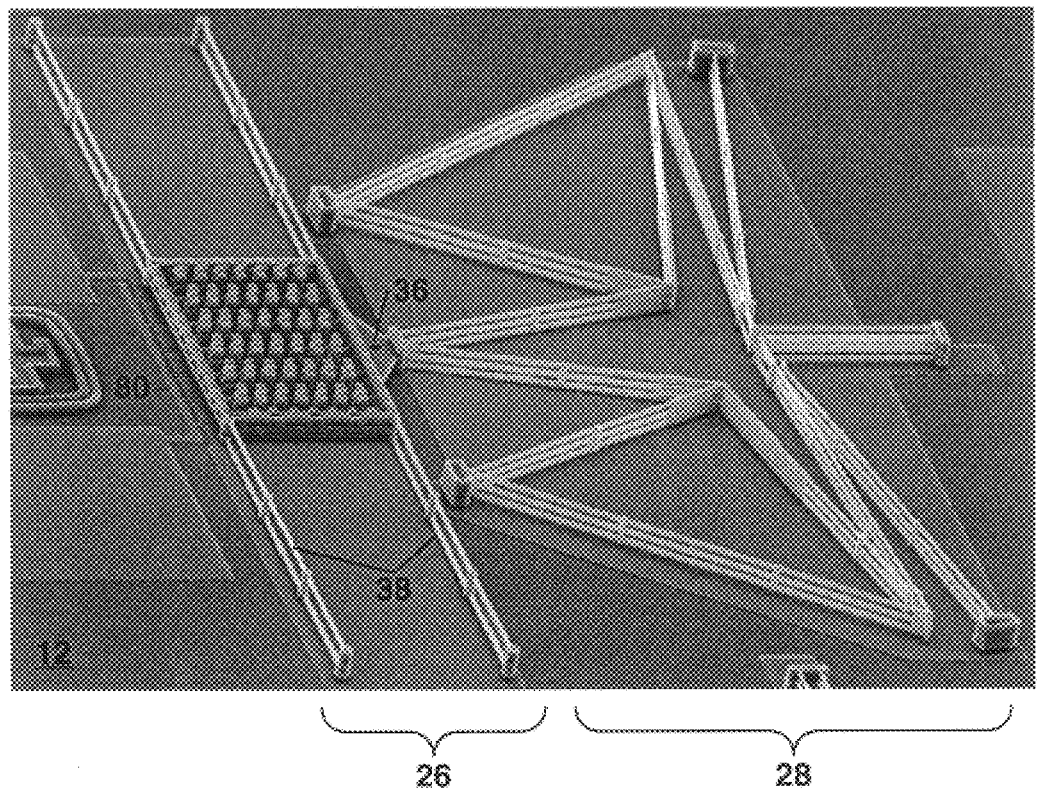
FIG. 7 shows a scanning electron microscope (SEM) image of the electrostatic actuator of FIG. 6 coupled to drive the compliant structure of FIG. 1.

FIG. 7 shows a scanning electron microscope image of this alternative type of the electrostatic actuator 26 coupled to drive the compliant structure 28 of FIG. 1. Further details of this alternative type of electrostatic actuator 26 can be found in U.S. patent application Ser. No. 09/615,008 which is incorporated herein by reference.

Those skilled in the art will understand that other types of electrostatic actuators including electrostatic comb actuators can also be used according to the present invention. Furthermore, those skilled in the art will understand that either unidirectional or bidirectional electrostatic actuators 26 can be used on the apparatus 10 of the present invention.

Figure 8:
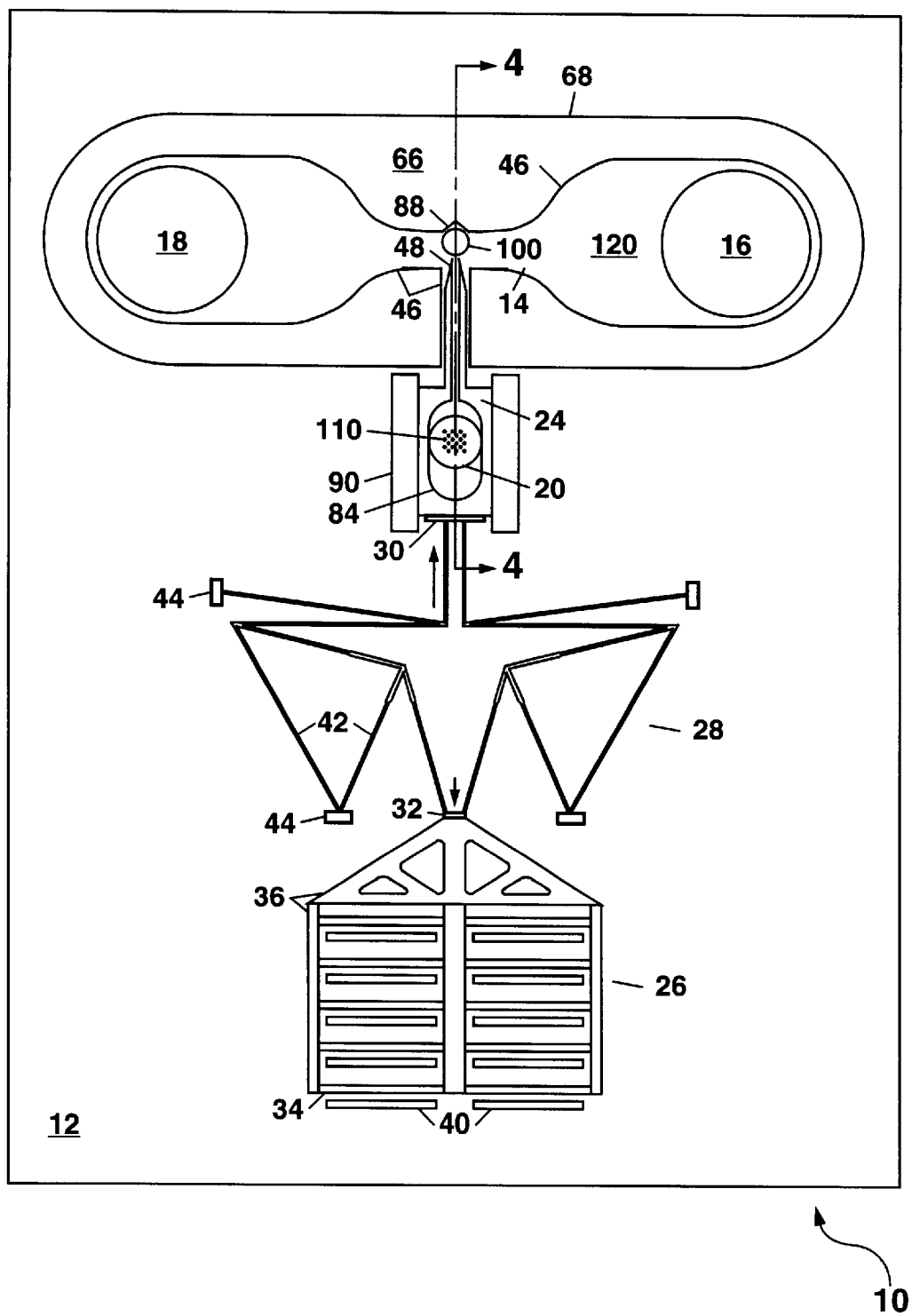
FIG. 8 shows a schematic plan view of a second embodiment of the cell transformation apparatus of the present invention.

FIG. 8 shows a second embodiment of the apparatus 10 of the present invention. In this embodiment of the apparatus 10, which can be fabricated by surface micromachining using the same process steps described previously with reference to FIGS. 2A–2L, the moveable member 24 comprises a hollow micromachined needle (i.e. a probe) for penetrating the host cell 100 and directly injecting therein the substance of interest 110. The moveable member 24 can be optionally covered with the silicon nitride 54, especially for portions of the moveable member 24 coming into contact with the fluid 120 or the host cell 100.

Figure 9:
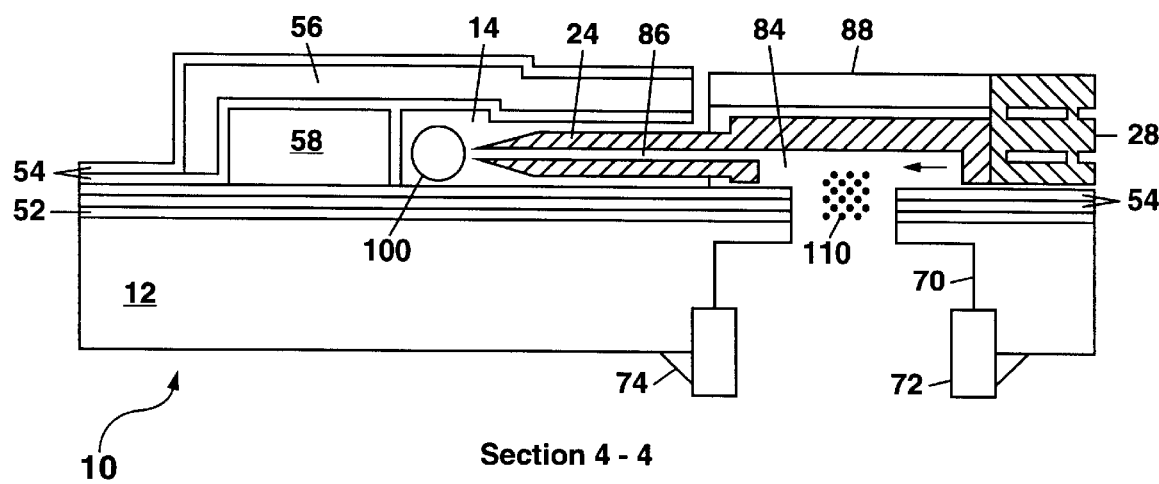
FIG. 9 schematically illustrates a cross-section view of the apparatus along the section line 4—4 in FIG. 8.

FIG. 9 shows a schematic cross-section view of this second embodiment of the apparatus 10 along the section line 4—4 in FIG. 8. The substance of interest 110 can be introduced into the moveable member 24 by locating an elongate cavity 84 in the moveable member 24 over the third port 20 as shown in FIGS. 8 and 9, with the sides of the cavity 84 being in sliding contact with the surface of the substrate 12. A conduit 86 (e.g. with a square or rectangular cross-section) can be formed through a pointed end of the moveable member 24 to convey the substance of interest 110 from the third port 20 into the flow channel 14 proximate to the host cell 100, or directly into the host cell 100.

The conduit 86 can be formed, for example, by etching a trench in one or more layers of the polysilicon 56 used to form the body of the moveable member 24; filling the trench with the sacrificial material 58; and depositing and patterning another layer of the polysilicon 56 to cover the sacrificial material 58 in the trench. The sacrificial material 58 can later be removed to complete formation of the conduit 86 using the selective etchant described previously with reference to FIG. 2L.

To aid in retaining the host cell 100 substantially immobile during penetration with a pointed end of the moveable member 24, the inside wall 46 of the flow channel 14 can be optionally shaped to form a recess 88 therein opposite this end of the moveable member 24. This recess 88 can be formed using the same steps used to form the conduit 86, although the recess 88 will generally need to be etched deeper in the polysilicon 56 than the trench used to form the conduit 86.

To maintain the moveable member 24 in sliding contact with the substrate 12, a guide 90 built up from the various layers of polysilicon 56 (or alternately layers of the silicon nitride 54) can be located on each side of the moveable member 24, with each guide 90 extending partway or entirely over the top of the moveable member 24 as shown in FIG. 8. The guide 90, which is attached to the substrate 12, can be used to limit any upward movement of the moveable member 24 to about 1 µm or less to prevent leakage of the substance of interest 110 and fluid 120 from the third port 20 onto the surface of the substrate 12.

The pointed end of the moveable member 24 adapted to penetrate the host cell 100 can have a size and shape that, in general, will be a fraction (e.g. one-tenth) of the size of the host cell 100 being transformed with the apparatus 10. For example, the pointed end of the moveable member 24 can be chisel-shaped (e.g. tapered on one or both sides in a horizontal direction parallel to the substrate 12), stair-stepped (e.g. stepped on one or both sides in the horizontal direction, or in a vertical direction perpendicular to the plane of the substrate 12, or both) or pyramidal (i.e. tapered in both the horizontal and vertical directions). The exact shape of the pointed end of the moveable member 24 will be determined during patterning of the various layers of the polysilicon 56 and sacrificial material 58 used to form the moveable member 24.

In addition to inserting substances of interest 110 into a host cell 100, this second embodiment of the present invention can be used to remove cellular material (e.g. DNA) from a host cell 100. This can be done by providing suction at the third port 20 after insertion of the pointed end of the moveable member 24 into the host cell 100. The removed cellular material can be recovered from the third port 20, for example, for transfecting other host cells 100. Alternately, the removed cellular material can be retained in the conduit 86 for later insertion into another host cell 100 of the same or different type for transformation thereof.

In other embodiments of the present invention, the moveable member 24 can comprise a solid micromachined needle for penetrating the host cell 100 to disrupt the integrity of the host cell 100 and thereby allow a substance of interest 110 in the fluid 120 surrounding the host cell 100 to enter therein. The solid needle can also be used to directly inject a substance of interest 110 into the host cell 100, with the substance of interest 110 being located on a surface of the needle, on the surface of the host cell 100, or in the fluid 120 between the needle and the host cell 100.

Figure 10:
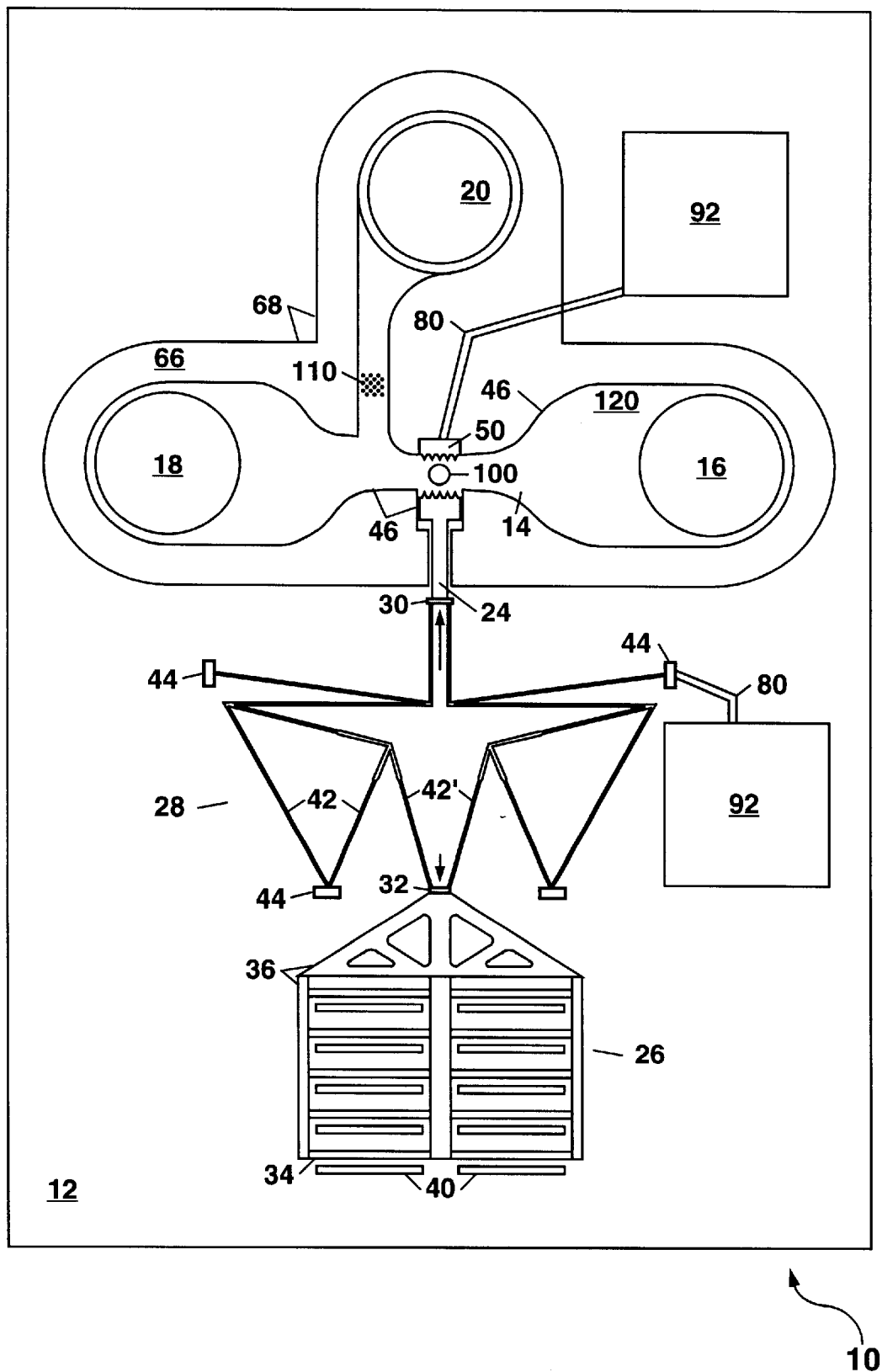
FIG. 10 shows a schematic plan view of a third embodiment of the cell transformation apparatus of the present invention.

A third embodiment of the apparatus 10 of the present invention shown in FIG. 10 combines mechanical and electrical means for temporarily disrupting the integrity of a host cell 100 thereby porating the host cell 100 so that a substance of interest 110 can be introduced therein. Mechanical and electrical poration of the host cell 100 can be performed separately in a predetermined sequence, or simultaneously.

This third embodiment of the present invention can be formed similarly to the first embodiment of FIG. 1 except that electrical connections are provided to the moveable member 24 and the stationary member 50 which form a pair of electrodes for generating an electrical field across the host cell 100 in response to a voltage applied therebetween. The actuation voltage can be provided by the same source or power supply used to activate the electrodes 22 and 22' in FIG. 1.

In FIG. 10, the electrical connection to the stationary member 50 can be through wiring 80 formed in the Poly-0 layer, with the stationary member 50 being electrically connected to a probe or bond pad 92. The moveable member 24 can be connected to ground electrical potential through the compliant structure 28 and the frame 36 of the electrostatic actuator 26 which are formed from electrically-conductive polysilicon 56 (i.e. polysilicon doped with phosphorous or boron for electrical conductivity). Surfaces of the moveable and stationary members, 24 and 50, that extend into the flow channel 14 can be optionally coated with a metal (e.g. gold, platinum or tungsten) or a metal alloy during fabrication thereof (e.g. for biocompatibility). The types of metals used to coat the surfaces of the moveable member 24 and the stationary member 50 can be different to prevent electrolysis.

Alternately, the moveable member 24 can be electrically isolated from the electrostatic actuator 26, for example, by forming some of the flexible beams (e.g. the beams 42' in FIG. 10) of the compliant structure 24 proximate to the input side 32 from electrically insulating silicon nitride 54 instead of polysilicon 56. If this is done, a separate electrical connection to the moveable member 24 can be formed through the moveable member 24 and certain of the flexible beams 42 electrically isolated from the electrostatic actuator 26 to one or more of the support posts 44 which can, in turn, be connected to wiring 80 formed in the Poly-0 layer and therefrom to a probe or bond pad 92. The probe or bond pads 92 allow external connections to be made to the apparatus 10 from an external source or power supply (not shown) which provides the actuation voltage to the electrodes formed from the members, 24 and 50, for electroporation of the host cell 100.

In the third embodiment of the present invention in FIG. 10, movement of the member 24 toward or away from the host cell 100 can be used to provide added flexibility in controlling the magnitude of the electric field to be generated across the host cell 100 for electroporation. The combination of mechanical and electrical poration provided by this embodiment of the apparatus 10 is expected to provide the user with added flexibility for transforming many different types of host cells 100, and may improve the efficiency of transformation compared to the use of mechanical poration or electroporation alone.

After transformation of one or more host cells 100 with the apparatus 10, the transient holes or pores in the cell membrane through which the substance of interest 110 has been enabled to enter into the cell 100 heal and re-close so that normal cell activity can continue as modified by the introduced substance 110. The transformed host cells 100 can be removed from the apparatus 10 through exit port 18.

Other applications and variations of the present invention will become evident to those skilled in the art. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. An apparatus for transforming a host cell, comprising:
   (a) a closed flow channel lined with silicon nitride for containing the host cell and a surrounding fluid; and
   (b) means, located at least partially within the flow channel, for temporarily disrupting the integrity of the host cell and thereby introducing a substance into the host cell for transforming the host cell, wherein the disrupting means comprises a movable member.

2. The apparatus of claim 1 wherein the flow channel and the disrupting means are formed on a common substrate.

3. The apparatus of claim 2 wherein the substrate comprises silicon.

4. The apparatus of claim 2 wherein the disrupting means further comprises a pair of electrodes located proximate to the host cell on opposite sides of the flow channel for generating an electric field across the host cell in response to a voltage applied between the pair of electrodes.

5. The apparatus of claim 4 wherein each electrode is pointed on one end or side thereof.

6. The apparatus of claim 1 wherein the moveable member is operatively connected to an electrostatic actuator formed on the substrate to provide motion thereto.

7. The apparatus of claim 6 wherein the motion is reciprocating motion.

8. The apparatus of claim 2 wherein the flow channel includes means for urging the host cell to move along the flow channel.

9. The apparatus of claim 2 further including an input port connected to one end of the flow channel for transferring the host cell and the fluid into the flow channel, and an exit port connected to the other end of the flow channel for transferring the host cell and the fluid out of the flow channel.

10. The apparatus of claim 9 further including a third port in fluid communication with the flow channel for introducing the substance to be transferred into the host cell into the fluid.

11. The apparatus of claim 1 wherein the disrupting means includes a conduit for transporting the substance from a third port into the flow channel or directly into the host cell.

12. An apparatus for transforming a host cell, comprising:
   (a) a closed flow channel formed on a substrate for isolating the host cell from a plurality of other host cells within a fluid surrounding the host cell; and
   (b) a moveable member formed on the substrate and located on one side of the flow channel for abrading, impacting or penetrating the host cell for transferring a substance into the host cell and thereby transforming the host cell.

13. The apparatus of claim 12 wherein an end or side of the moveable member that abrades, impacts or penetrates the host cell is pointed or serrated.

14. The apparatus of claim 13 further including a stationary member located opposite the moveable member, with the stationary member being pointed or serrated on a side thereof facing the host cell.

15. The apparatus of claim 14 wherein the moveable and stationary members form electrodes for applying a voltage across the host cell to further condition the host cell for receiving the substance to be transferred therein.

16. The apparatus of claim 12 wherein the flow channel is lined with silicon nitride.

17. The apparatus of claim 12 wherein the flow channel includes a plurality of electrodes therein for generating a flow of the fluid along the flow channel in response to a voltage applied between the electrodes.

18. The apparatus of claim 12 further including an electrostatic actuator operatively connected to the moveable member for providing motion thereto.

19. The apparatus of claim 18 wherein the electrostatic actuator is operatively connected to the moveable member through a linkage comprising a compliant structure.

20. The apparatus of claim 19 wherein the compliant structure provides a stroke for the moveable member that is larger than the stroke provided by the electrostatic actuator.

21. The apparatus of claim 12 further including an input port connected to one end of the flow channel for admitting the host cell and the fluid into the flow channel, and an exit port connected to the other end of the flow channel for transferring the host cell and the fluid out of the flow channel.

22. The apparatus of claim 21 of further including a third port in fluid communication with the flow channel for admitting the substance to be transferred to the host cell into the fluid.

23. The apparatus of claim 21 wherein the moveable member includes a conduit for transporting the substance from a third port into the flow channel or directly into the host cell.

24. The apparatus of claim 12 wherein the substrate comprises silicon.

25. An apparatus for transforming a host cell, comprising:
   (a) a flow channel for isolating the host cell from a plurality of other host cells in a fluid, with the fluid further including a substance to be transferred into the host cell for transforming the host cell;

(b) a stationary electrode located on one side of the flow channel; and (c) a moveable electrode located on the other side of the flow channel opposite the stationary electrode, the stationary and moveable electrodes being adapted to provide a voltage across the host cell when the host cell is positioned between the electrodes for conditioning the host cell to receive the substance to be transferred therein.

26. The apparatus of claim 25 wherein the flow channel is formed on a substrate.

27. The apparatus of claim 26 wherein the substrate comprises silicon.

28. The apparatus of claim 25 wherein the flow channel is lined with silicon nitride.

29. The apparatus of claim 25 wherein at least one of the stationary and moveable electrodes is sharpened to provide a pointed or serrated edge facing the host cell.

30. The apparatus of claim 25 wherein the stationary and moveable electrodes comprise polysilicon.

31. The apparatus of claim 25 further comprising an electrostatic actuator for providing motion to the moveable electrode.

32. The apparatus of claim 31 wherein the motion provided to the moveable electrode is a reciprocating motion in a direction substantially perpendicular to the flow channel.

33. The apparatus of claim 31 wherein the electrostatic actuator is connected to the moveable electrode by a linkage.

34. The apparatus of claim 33 wherein the linkage comprises a compliant structure.

35. The apparatus of claim 25 wherein the flow channel includes means for urging the host cell to move along the flow channel.

36. The apparatus of claim 35 wherein the urging means comprises a pressure gradient in the fluid along the channel, thereby producing a flow of the fluid surrounding the host cell.

37. The apparatus of claim 35 wherein the urging means comprises at least one additional electrode located in the flow channel on each side of the stationary electrode.

38. The apparatus of claim 37 wherein an applied voltage provided between the additional electrodes on each side of the stationary electrode generates a flow of the fluid surrounding the host cell, thereby urging the host cell to move along the channel.

39. The apparatus of claim 25 further including a first port connected to one end of the flow channel for admitting the host cell and the fluid into the flow channel, and a second port connected to the other end of the flow channel for transferring the host cell and the fluid out of the flow channel.

40. The apparatus of claim 39 further including a third port in fluid communication with the flow channel for introducing the substance to be transferred into the host cell into the fluid.

41. The apparatus of claim 25 wherein the substance to be transferred into the host cell is selected from the group consisting of biological stains, proteins, nucleic acids, antibodies, organelles, chromosomes, nuclei, viruses, plasmids and bacteria.

42. A method for transforming a host cell, comprising steps for:

(a) immersing the host cell in a fluid and introducing the fluid and host cell into a closed flow channel;

(b) positioning the host cell adjacent to a moveable member extending into the flow channel through a sidewall thereof; and (c) abrading, impacting or penetrating the host cell with the moveable member thereby temporarily disrupting the integrity of the host cell and forming a pathway for a substance of interest to enter the host cell for transforming the host cell.

43. The method of claim 42 further including a step for generating an electric field across the host cell by applying a voltage between a pair of electrodes located on opposite sides of the flow channel.

* * * * *